United States Patent [19]

Travers et al.

[11] Patent Number: 4,514,515

[45] Date of Patent: Apr. 30, 1985

[54] PROCESS FOR MANUFACTURING A CATALYST COMPRISING RHODIUM AND AT LEAST ONE METAL SELECTED FROM THE GROUP CONSISTING OF TIN, GERMANIUM AND LEAD AND THE CATALYST PRODUCED BY THE PROCESS

[75] Inventors: Christine Travers, Rueil-Malmaison; Trinh D. Chan, Le Vesinet; Roger Snappe, Sevres; Jean-Paul Bournonville, Chatou, all of France

[73] Assignee: Institut Francais du Petrole, Rueil-Malmaison, France

[21] Appl. No.: 597,288

[22] Filed: Apr. 6, 1984

Related U.S. Application Data

[63] Continuation-in-part of Ser. No. 497,631, May 24, 1983, Pat. No. 4,456,775.

[30] Foreign Application Priority Data

May 24, 1982 [FR] France .................................. 8209099

[51] Int. Cl.³ .......................... B01J 21/04; B01J 21/08; B01J 23/62
[52] U.S. Cl. ..................................... 502/154; 502/242; 502/325; 502/332
[58] Field of Search ................. 502/325, 332, 242, 154

[56] References Cited

U.S. PATENT DOCUMENTS

| | | | |
|---|---|---|---|
| 3,794,599 | 2/1974 | Dautzenberg et al. | 502/332 X |
| 3,825,503 | 7/1974 | Patrick et al. | 502/304 |
| 4,104,478 | 8/1978 | Trivedi | 568/885 |
| 4,338,221 | 7/1982 | Qualeatti | 502/341 X |

Primary Examiner—W. J. Shine
Attorney, Agent, or Firm—Millen & White

[57] ABSTRACT

A catalyst comprising a carrier, rhodium and at least one element selected from the group consisting of tin, germanium and lead is prepared from a rhodium compound and an alkyl, cycloalkyl or aryl tin, germanium or lead compound.

25 Claims, No Drawings

PROCESS FOR MANUFACTURING A CATALYST COMPRISING RHODIUM AND AT LEAST ONE METAL SELECTED FROM THE GROUP CONSISTING OF TIN, GERMANIUM AND LEAD AND THE CATALYST PRODUCED BY THE PROCESS

This application is a continuation-in-part of our patent application Ser. No. 497,631 filed May 24, 1983, now U.S. Pat. No. 4,456,775 issued June 26, 1984.

This invention relates to the manufacture of a catalyst comprising rhodium and at least one metal selected from the group consisting of tin, germanium and lead.

This catalyst may find use in a number of hydrogenation reactions. Examples thereof are hydrogenations of unsaturated compounds and hydrogenolysis reactions. A preferred use is the manufacture of alcohols by hydrogenolysis of carboxylic esters.

BACKGROUND OF THE INVENTION

The manufacture of alcohols, particularly of fatty alcohols, is of great industrial significance.

The catalytic hydrogenolysis of carboxylic esters is an attractive manner of manufacturing these alcohols; however it has been limited up to now by the poor performances of the known catalysts:

the catalysts comprising mixed copper and chromium oxides, with or without additives, require working under high pressure, in nearly all cases above 200 atmospheres, and at a temperature of 250° to 350° C., the catalysts comprising supported transition metals are required to operate at a temperature lower than 250° C. and preferably lower than 200° C., to limit the degradation of the resultant alcohol to hydrocarbons, which requires operating pressures above 100 bars to obtain good selectivities at an acceptable conversion level.

Catalyst comprising rhodium and tin or lead on silica are disclosed in Chemical Abstracts, vol. 93, Nov. 25, Dec. 22, 1980, page 761, No. 238,371 s; lead and silica were supplied in ionic form.

U.S. Pat. No. 3,825,503 discloses a rhodium-tin catalyst obtained from water-soluble soluble metal salts.

DE No. 3 019 582 discloses a method for manufacturing catalysts comprising both noble and non-noble metals; water-soluble metal salts are used.

SUMMARY OF THE INVENTION

It has surprisingly been discovered that the hydrogenation of an ester to an alcohol can be performed without structural modification of the hydrocarbon chain, according to the following scheme:

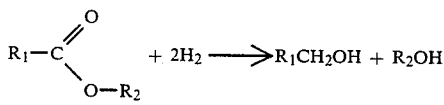

where $R_1$ = saturated or unsaturated hydrocarbyl radical of 1-20 carbon atoms and $R_2$ = alkyl of 1-10 carbon atoms, preferably methyl or ethyl, provided there is used a catalyst obtained by admixing a carrier with a rhodium compound and at least one compound selected from the group consisting of the alkyl, cycloalkyl and aryl tin, germanium and lead compounds. The operation is preferably performed in a continuous or a batch reactor under a total pressure of 10 to 100 bars, preferably 30 to 80 bars, although the pressure can be as high as 300 bars, without disadvantage, at a temperature of 180° to 330° C. and preferably 200° to 280° C. and with a hydrogen to ester molar ratio of 2 to 10, more advantageously 2 to 5.

The catalyst comprises the following elements: rhodium, in a proportion b.w. from 0.1 to 5% and preferably from 0.5 to 2%, and at least one germanium, tin and/or lead compound as hereinbefore defined in a proportion from 0.1 to 10% and more particularly from 2 to 5%, calculated as metal.

Two of the above metals or even these three metals can advantageously be used together; the carrier can be selected from the group consisting of silica, different types of alumina, silicaaluminas, coal, and preferably from the group of the different aluminas. The use of an alumina carrier containing 1-5% of alkali metal (Na, K) or alkaline-earth metal (Mg, Ca, Ba) is also contemplated.

The catalyst can be prepared by different techniques of carrier impregnation and the invention is not limited to a particular technique. The impregnation operation consistss, for example, of contacting the preformed carrier with an aqueous or organic solution of the rhodium compound, the volume of solution being in excess to the absorption volume of the carrier or equal to this volume. Rhodium and the additional metal can be introduced simultaneously or successively. After having contacted the carrier with the solution for several hours, the impregnated carrier is filtered, washed with distilled water, dried and calcined in the air at 110° to 600° C. and preferably 110° to 500° C. Before use, the catalyst is reduced under hydrogen at 200°-600° C. and preferably 300°-500° C., this reduction being effected immediately after the calcination or later, by the user.

The tin, germanium or lead compound may be introduced in hydrocarbon solution. It is preferred to introduce rhodium first and to calcine or calcine and reduce, under the conditions described above, and to thereafter introduce the tin, germanium and/or lead compound.

Another method consists of malaxing the wet carrier powder with the catalyst precursors and to shape and dry thereafter.

Examples of metal precursors for use in the manufacture of the catalyst are the following:

Rhodium can be used as compounds, such as chlorides, nitrates or salts of organic acids soluble in the impregnation solvent, for example rhodium chloride, rhodium nitrate, soluble salts of organic acids such as rhodium acetate, or alternatively hexammine rhodium chloride or nitrate. Organometal compounds of rhodium can also be used as a solution in a hydrocarbon, for example in a saturated paraffinic hydrocarbon whose hydrocarbon chain comprises 6 to 12 carbon atoms, in a naphthenic hydrocarbon comprising 6 to 12 carbon atoms or in an aromatic hydrocarbon comprising 6 to 11 carbon atoms; preference will be given to rhodium acetylacetonate.

The element selected from the group consisting of tin, germanium and lead is introduced in the form of tin, germanium and lead alkyl-, cycloalkyl-or aryl-metals, such as, for example: tetrabutyl tin, tetramethyl tin, tetrapropyl germanium, tetraethyl lead, diphenyl tin, diphenyl germanium or tetraphenyl lead, in hydrocarbon solution.

The carrier may be of various types, as hereinbefore mentioned. A particularly well adapted carrier has the following specific characteristics: a specific surface, determined by the B.E.T. method, between 10 and 500 sq. m. per gram and preferably between 50 and 500 sq. m. per gram and a total pore volume between 20 and 130 $cm^3$ per 100 g of carrier and preferably between 50 and 110 $cm^3$ per 100 g of carrier.

Once the two metals have been attached to the carrier, the catalyst is usefully subjected to an activation treatment under hydrogen at a high temperature, for example 300°–500° C., in order to obtain an active metal phase. This treatment under hydrogen can be conducted, for example, by slowly increasing the temperature, under hydrogen stream, up to the maximum reduction temperature, comprised for example between 300° and 500° C. and preferably between 350° and 450° C., and thereafter maintaining this temperature for 1 to 6 hours.

The following non-limitative examples illustrate the invention.

EXAMPLE 1

The catalyst is manufactured in two steps:

adding rhodium by impregnating alumina with an aqueous solution of rhodium trichloride, this alumina having a specific surface of 200 $m^2$ per gram and a total pore volume of 60 $cm^3$ per 100 grams, followed with filtration, drying at 110° C., calcining at 450° C. in the air and reducing with hydrogen at 450° C., fixing tin onto the carrier preimpregnated with rhodium, calcined and reduced, as tetraethyl tin dissolved in n-heptane. After having contacted the catalyst with the tetraethyl tin solution at the heptane reflux for 4 hours, the catalyst is washed with heptane and dried.

The catalyst is then introduced into a tubular reactor and reduced for 4 hours at 300° C. in a hydrogen stream.

The operating conditions of the ethyl acetate hydrolysis are the following:
pressure : 50 bars
VVH : 4 1/1 of catalyst/hour
$H_2$/ester molar ratio : 5

In this first test series, the tin content of the catalysts has been varied from a basic catalyst containing 1% b.w. of rhodium. The working temperature was 250° C. The results are given in Table 1.

TABLE 1

| Rh (% b.w.) | Sn (% b.w.) | TOTAL CONVERSION (% b.w.) | YIELD (ETHANOL) (% b.w.) |
| --- | --- | --- | --- |
| 1 | 0 | 92 | 2.0 |
| 1 | 0.5 | 3 | 2.2 |
| 1 | 0.8 | 6 | 5.5 |
| 1 | 1.5 | 13.6 | 12.8 |
| 1 | 2.3 | 25.6 | 22.1 |
| 1 | 3.2 | 31.6 | 30.7 |

EXAMPLE 2

The catalytic properties of two catalysts have been compared at different temperatures with respect to the hydrogenolysis of ethyl acetate: one of them comprised 1% of rhodium on alumina, according to example 1, the other one comprised 1% of rhodium and 3.2% of tin on the same alumin carrier. The other conditions were those of example 1.

The results are given in Table 2.

TABLE 2

| TEMPERATURE °C. | CATALYST | | | |
| --- | --- | --- | --- | --- |
| | 1% Rh/$Al_2O_3$ | | 1% Rh + 3.2% Sn $Al_2O_3$ | |
| | CONVERSION % b.w. | YIELD (ETHANOL) % b.w. | CONVERSION % b.w. | YIELD (ETHANOL) % b.w. |
| 200 | 2.6 | 1.7 | 6.6 | 6.5 |
| 220 | 19.4 | 6.0 | 16.0 | 15.8 |
| 250 | 92 | 2.0 | 31.6 | 30.7 |
| 280 | 100 | 0 | 70.7 | 66.3 |

In the whole temperature range, it is found that the bimetallic rhodium-tin on alumina catalyst is far more selective for the alcohol production.

EXAMPLE 3

The object is to manufacture ethanol from ethyl acetate in the same conditions as in example 1. The catalyst comprises 1% rhodium on the alumina of example 1 and a second element of the group: tin, germanium and lead.

Germanium and lead are introduced by impregnation from respectively tetraethyl germanium and tetraethyl lead as a solution in a hydrocarbon (n-heptane).

The resultant catalysts are used in the same manner as in example 1 (T=250° C., P=50 bars, VVH=4, $H_2$/ester molar ratio=5).

The results are given in Table 3.

TABLE 3

| Rh (% b.w.) | SECOND METAL (% b.w.) | CONVERSION (% b.w.) | YIELD (ETHANOL) (% b.w.) |
| --- | --- | --- | --- |
| 1 | 0 | 92 | 2.0 |
| 1 | Sn = 3.2 | 31.6 | 30.7 |
| 1 | Ge = 3.1 | 30.9 | 30.5 |
| 1 | Pb = 3.4 | 31.9 | 30.6 |

Tin can thus be replaced with germanium and lead without significant alteration of the catalytic properties of the active mass.

EXAMPLE 4

There are prepared, according to the method of example 1, catalysts comprising rhodium and tin on silica having a specific surface of 450 $m^2$/g and a total pore volume of 80 $cm^3$ per 100 grams. The hydrogenolysis of ethyl acetate has been effected under conditions identical to those of example 1.

The results are given in Table 4.

TABLE 4

| RHODIUM (% b.w.) | TIN (% b.w.) | CONVERSION (% b.w.) | YIELD (ETHANOL) (% b.w.) | SELECTIVITY (ETHANOL) (% b.w.) |
| --- | --- | --- | --- | --- |
| 1 | 0 | 7 | 2.2 | 31.5 |
| 1 | 0.8 | 8.6 | 8.4 | 97.7 |
| 1 | 1.5 | 17.4 | 17.0 | 97.7 |
| 1 | 3.0 | 11.1 | 10.7 | 96.3 |

The selectivities of the conversion to alcohol are very high, in all cases higher than 95%.

EXAMPLE 5

A number of alcohols are manufactured from various esters in the presence of a catalyst (1% Rh+3.2% Sn+1.5% K on alumina) and under operating conditions identical to those of example 1.

The esters are the following:

sec. butyl acetate
amyl acetate
hexyl acetate
ethyl caprate
methyl palmitate
methyl oleate.

The results are summarized in Table 5.

TABLE 5

| SUBSTRATE | RESULTANT ALCOHOLS | CON-VERSION (% b.w.) | ALCOHOLS YIELD (% b.w.) |
|---|---|---|---|
| Sec. butyl acetate | Ethanol and 2-butanol | 30.5 | 29.0 |
| Isoamyl acetate | Ethanol and isoamyl alcohol | 33.0 | 31.5 |
| Hexyl acetate | Ethanol and 1-hexanol | 32.0 | 30.0 |
| Ethyl caprate | 1-decanol and ethanol | 35.0 | 33.1 |
| Methyl palmitate | 1-hexadecanol and methanol | 32 | 30.5 |
| Methyl oleate | 1-octadecanol and methanol | 34 | 32.8 |

EXAMPLE 6

Two catalysts were tested under the conditions of example 1 for ethyl acetate hydrogenolysis.

One (catalyst A) was the catalyst prepared from rhodium trichloride and tetra-ethyl tin as disclosed in example 1; this catalyst contained 1% b.w. of rhodium and 3.2% b.w. of tin.

The other one (catalyst B) had the same contents of rhodium and tin and was prepared from the same alumina; rhodium was introduced as disclosed in example 1 with the same steps of impregnating, filtering, drying, calcining and reducing. Tin was introduced thereafter from an acetonic solution of tin dichloride, followed with filtering, washing with acetone, drying and reducing for 4 hours in a hydrogen stream at 300° C.

The results were as summarized in Table 6.

TABLE 6

| Catalyst | Total conversion % b.w. | Ethanol yield % b.w. |
|---|---|---|
| A | 31.6 | 30.7 |
| B | 9.5 | 8.1 |

These results clearly show the improved results obtained with the catalyst prepared from tetra-ethyl tin instead of tin dichloride.

What is claimed is:

1. A process for manufacturing a catalyst comprising rhodium and at least one of tin, germanium and lead, comprising admixing a carrier with a rhodium compound and at least one metal compound selected from the group consisting of the alkyl, cycloalkyl and aryl tin, germanium and lead compounds.

2. A process according to claim 1, wherein the rhodium compound and the tin, germanium and lead compounds are used in sufficient proportions to provide the catalyst with 0.1 to 5% by weight of rhodium and 0.1 to 10% by weight of the metal selected from the group consisting of tin, germanium and lead.

3. A process according to claim 1, wherein the rhodium compound and the tin, germanium and lead compounds are used in sufficient proportions to provide the catalyst with 0.5 to 2% by weight of rhodium and 2 to 5% by weight of the metal selected from the group consisting of tin, germanium and lead.

4. A process according to claim 1 wherein the carrier has a surface area of 10 to 500 $m^2/g$ and a pore volume of 0.2 to 1.3 $cm^3/g$.

5. A process according to claim 1, wherein the carrier has a surface area of 50 to 500 $m^2/g$ and a pore volume of 0.5 to 1.1 $cm^3/g$.

6. A process according to claim 1, wherein the carrier is alumina.

7. A process according to claim 1, wherein the carrier is silica.

8. A process according to claim 1, wherein said admixing is performed by admixing the carrier with a solution of said rhodium compound, drying, calcining at 110°–600° C., and then admixing with a hydrocarbon solution of said compound selected from the group consisting of the tin, germanium and lead compounds.

9. A process according to claim 8, wherein said calcining at 110°–600° C. is followed with reducing with hydrogen at 200°–600° C., before said admixing with said hydrocarbon solution.

10. A process according to claim 8, wherein said admixing with said hydrocarbon solution is followed with activation in hydrogen at 300°–500° C.

11. A process according to claim 8, wherein the carrier is alumina having a specific surface area of 10–500 $m^2/g$ and a pore volume of 0.2–1.3 $cm^3/g$.

12. A process according to claim 8, wherein the rhodium compound is rhodium trichloride.

13. A process according to claim 8, wherein the compound selected from the group consisting of the tin, germanium and lead compounds is an alkyl tin compound.

14. A process according to claim 10, wherein said activation in hydrogen is performed at 350°–450° C. for 1–6 hours.

15. A catalyst produced according to the process of claim 8.

16. A catalyst produced according to the process of claim 9.

17. A catalyst produced according to the process of claim 10.

18. A catalyst produced according to the process of claim 11.

19. A catalyst produced according to the process of claim 12.

20. A catalyst produced according to the process of claim 13.

21. A catalyst produced according to the process of claim 14.

22. A process according to claim 1, wherein a solution of the rhodium compound is employed.

23. A catalyst produced by the process of claim 22.

24. A process of activating a catalyst comprising rhodium and at least one of tin, germanium and lead, said catalyst having been produced by admixing a carrier with a rhodium compound and at least one metal compound selected from the group consisting of the alkyl, cycloalkyl and aryl tin, germanium and lead compounds, said activating process comprising reducing said catalyst with hydrogen at 200°–600° C.

25. An activated catalyst produced by the process of claim 24.

* * * * *